United States Patent
Moszner et al.

(10) Patent No.: US 10,857,073 B2
(45) Date of Patent: Dec. 8, 2020

(54) DENTAL MATERIALS BASED ON LOW-VISCOSITY RADICALLY POLYMERIZABLE MONOMERS WITH A HIGH REFRACTIVE INDEX

(71) Applicant: Ivoclar Vivadent AG, Schaan (LI)

(72) Inventors: Norbert Moszner, Mauren (LI); Urs Karl Fischer, Arbon (CH); Pascal Fässler, Sargans (CH)

(73) Assignee: Ivoclar Vivadent AG, Schaan (LI)

( * ) Notice: Subject to any disclaimer, the term of this patent is extended or adjusted under 35 U.S.C. 154(b) by 176 days.

(21) Appl. No.: 16/032,382

(22) Filed: Jul. 11, 2018

(65) Prior Publication Data

US 2019/0015301 A1    Jan. 17, 2019

(30) Foreign Application Priority Data

Jul. 14, 2017    (EP) .................................... 17181491

(51) Int. Cl.
| | | |
|---|---|---|
| A61K 6/083 | (2006.01) | |
| A61K 6/887 | (2020.01) | |
| A61K 6/842 | (2020.01) | |
| A61K 6/853 | (2020.01) | |
| C07C 321/30 | (2006.01) | |
| C08F 228/02 | (2006.01) | |

(52) U.S. Cl.
CPC .............. *A61K 6/887* (2020.01); *A61K 6/842* (2020.01); *A61K 6/853* (2020.01); *C07C 321/30* (2013.01); *C08F 228/02* (2013.01); *C08F 2800/20* (2013.01)

(58) Field of Classification Search
CPC ................................ A61K 6/083; A61K 6/887
See application file for complete search history.

(56) References Cited

U.S. PATENT DOCUMENTS

| | | |
|---|---|---|
| 4,291,047 A | 9/1981 | Kranz et al. |
| 4,447,520 A | 5/1984 | Henne et al. |
| 4,737,593 A | 4/1988 | Ellrich et al. |
| 5,183,917 A * | 2/1993 | Maruyama ............ C07C 327/22 558/251 |
| 5,534,559 A | 7/1996 | Leppard et al. |
| 2008/0076847 A1 | 3/2008 | Moszner et al. |
| 2008/0200582 A1* | 8/2008 | Craciun ............ B29D 11/00442 522/166 |
| 2010/0076106 A1* | 3/2010 | Iwasa ....................... G02B 1/04 522/44 |
| 2011/0026118 A1 | 2/2011 | Seesselberg et al. |

FOREIGN PATENT DOCUMENTS

JP    H08157320 A    6/1996

OTHER PUBLICATIONS

Elias, H.-G., "Macromolecules," Applications of Polymers, vol. 4, pp. 619-620, 2003. WILEY-VCH Verlag GmbH & Co. KGaA.

* cited by examiner

*Primary Examiner* — Michael F Pepitone
(74) *Attorney, Agent, or Firm* — Ann M. Knab; Thad McMurray

(57) ABSTRACT

Radically polymerizable, difunctional phenylene sulfide according to Formula I

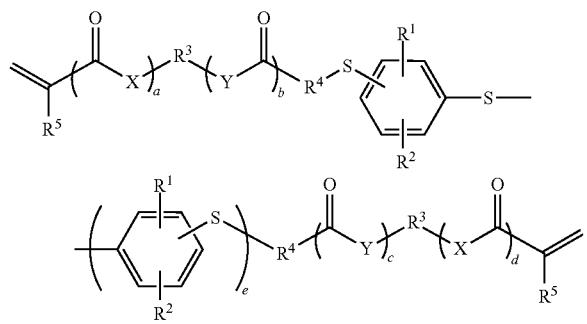

Formula I in which X, Y independently of each other in each case are absent or are O or $NR^6$, $R^1$, $R^2$ independently of each other in each case are H, a linear or branched $C_1$ to $C_{10}$ alkyl radical, $-OR^7$, $-SR^8$, Cl or Br, $R^3$ is absent or is a $C_1$-$C_{10}$ alkylene radical which can be interrupted by O or S, $R^4$ is absent or is a $C_1$-$C_{10}$ alkylene radical which can be interrupted by O or S, wherein $R^3$ and $R^4$ cannot be absent at the same time, $R^5$ is H or a $C_1$-$C_5$ alkyl radical, $R^6$, $R^7$, $R^8$ independently of each other in each case are H or a linear or branched $C_1$ to $C_{10}$ alkyl radical, a, b, c, d independently of each other in each case are 0 or 1 and e is 1 or 2.

17 Claims, No Drawings

DENTAL MATERIALS BASED ON LOW-VISCOSITY RADICALLY POLYMERIZABLE MONOMERS WITH A HIGH REFRACTIVE INDEX

CROSS-REFERENCE TO RELATED APPLICATIONS

This application claims priority to European patent application No. 17181491.6 filed on Jul. 14, 2017, the disclosure of which is incorporated herein by reference in its entirety.

TECHNICAL FIELD

The present invention relates to dental materials based on low-viscosity radically polymerizable monomers with a high refractive index which are particularly suitable as dental cements and filling composites and for the production of shaped bodies.

BACKGROUND

Dental materials which are used e.g. as cement or as direct filling material, as a rule, contain a polymerizable organic matrix and one or more fillers, which are usually surface-modified with a polymerizable adhesion promoter. The filler content substantially depends on the desired intended use and can be up to 90 wt.-%, wherein fixing cements have a lower filling level than filling materials. The polymerizable organic matrix normally contains a mixture of monomers, initiator components, stabilizers and pigments. Dental materials which contain a polymerizable matrix and filler are called composites. The polymerizable matrix is also called resin.

Mixtures of dimethacrylates are usually used as monomers. Common examples of these are the high-viscosity dimethacrylates 2,2-bis[4-(2-hydroxy-3-methacryloyloxy-propyl)phenyl]propane (Bis-GMA) and 1,6-bis-[2-methacryloyloxyethoxycarbonylamino]-2,2,4-trimethylhexane (UDMA) and the lower-viscosity dimethacrylates bis-(3-methacryloyloxymethyl)tricyclo-[5.2.1.0$^{2,6}$]decane (TCP), decanediol-1,10-dimethacrylate (D$_3$MA) and triethylene glycol dimethacrylate (TEGDMA) which are used as diluent monomers. During polymerization, dimethacrylates bring about a three-dimensional crosslinking of the polymer chains that form and thus result in an improved mechanical stability.

The materials normally also contain an initiator for the radical polymerization, wherein light-curing materials, which contain a photoinitiator, are now adopting a dominant position in dental restoration.

A disadvantage of light-curing materials is that, in particular, fitting large fillings is associated with a substantial effort because the light needed for the curing can only penetrate into the materials up to a limited depth. In the so-called increment technique the filling is therefore built up in layers of the composite material, wherein the layers have a thickness of approximately 2 mm in each case and are cured individually.

Recently, so-called "bulk-fill" composites which allow layer thicknesses of from 4 to 5 mm have found broad interest because of the possible time saving. A prerequisite for the clinical suitability of these materials is a large curing depth.

The curing depth is dependent both on process parameters and on the material properties. There is thus, e.g., a logarithmic relationship between the curing depth and the intensity of the irradiated light or the exposure time. Furthermore, the curing depth correlates with the transparency and translucence of the materials. Translucence is usually referred to instead of transparency (diaphaneity) in the case of filler-containing materials because, although they allow light to pass through, as a rule they are not transparent. Bodies with a light transmission of less than 90% are referred to as translucent in the art.

In the ideal case (no absorption and refraction), the light transmission of polymers is dependent on their refractive index n and varies between 98.4% (n=1.29) and 92.8% (n=1.73) (cf. H.-G. Elias, Makromoleküle—Anwendungen von Polymeren, vol. 4, 6$^{th}$ edition, Wiley-VCH, Weinheim 2003, 517). However, these ideal values are only rarely achieved, because the light is scattered and absorbed.

The light transmission of composites is influenced, among other things, by the refractive indices of the resin matrix and of the fillers, by the size of the filler particles (scattering) as well as the type and concentration of added dyestuffs (absorption). The refractive index of particularly frequently used dental monomers decreases in the following order: Bis-GMA (1.5512), ethoxylated Bis-GMA (SR-348c) (1.5393), UDMA (1.4850), TEGDMA (1.4610) and D$_3$MA (1.4600). The refractive index of the X-ray-opaque glasses frequently used as filler lies in the range of 1.523-1.550 and the refractive index of dental enamel is 1.655.

In the case of composites, a high light transmission and thus a good curing depth can be achieved by using an organic matrix and fillers with matching refractive indices. Aromatic methacrylates often have high refractive indices, which approximately correspond to the refractive indices of X-ray-opaque glasses. On the other hand, such monomers often have a high viscosity and can be processed and mixed with fillers only after the addition of low-viscosity monomers. The diluent monomers usually used in the dental field, such as TEGDMA or D$_3$MA, however, have only relatively low refractive indices, usually far below 1.50, with the result that the addition thereof brings about a reduction in the refractive index of the resin mixture and thus an impairment of the light transmission.

SUMMARY OF THE INVENTION

The object of the invention is to provide light-curable materials which are suitable in particular for dental purposes and which have a great curing depth and a low polymerization shrinkage.

DETAILED DESCRIPTION

This object is achieved according to the invention by materials which contain at least one radically polymerizable, difunctional phenylene sulfide according to general formula I,

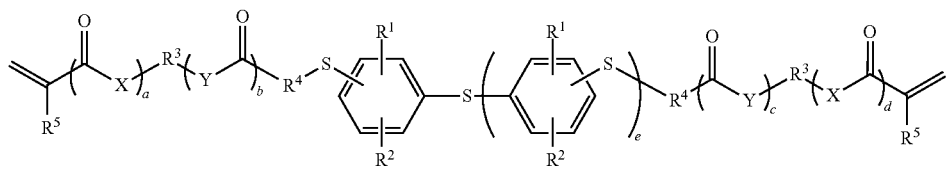

Formula I in which
X, Y independently of each other in each case are absent or are O or NR$^6$,
R$^1$, R$^2$ independently of each other in each case are H, a linear or branched C$_1$ to C$_{10}$ alkyl radical, —OR$^7$, —SR$^8$, Cl or Br,
R$^3$ is absent or is a C$_1$-C$_{10}$ alkylene radical, which can be interrupted by O or S,
R$^4$ is absent or is a C$_1$-C$_{10}$ alkylene radical, which can be interrupted by O or S, wherein R$^3$ and R$^4$ cannot be absent at the same time,
R$^5$ is H or a C$_1$-C$_5$ alkyl radical,
R$^6$, R$^7$, R$^8$ independently of each other in each case are H or a linear or branched C$_1$ to C$_{10}$ alkyl radical,
a, b, c, d independently of each other in each case are 0 or 1 and
e is 1 or 2.

Compounds in which a=d and b=c are preferred. If R$^3$ is absent, X or Y is preferably also absent, particularly preferably X and Y are absent.

Formula I only extends to those compounds which are compatible with the chemical valence theory. The indication that a radical is interrupted by one or more O atoms or S atoms is to be understood such that these atoms in each case are inserted into the carbon chain of the radical. These atoms are thus bordered on both sides by C atoms and cannot be terminal. C$_1$ radicals cannot be interrupted.

Difunctional phenylene sulfides of Formula I, wherein at least one variable has one of the following meanings, are preferred:
X, Y independently of each other in each case are absent or are O,
R$^1$, R$^2$ independently of each other in each case are H or Br, CH$_3$, SCH$_3$, OCH$_3$,
R$^3$ is absent or is a C$_2$-C$_4$ alkylene radical,
R$^4$ is absent or is a C$_1$-C$_3$ alkylene radical,
R$^5$ is H or CH$_3$,
a, b, c, d independently of each other in each case are 0 or 1, and
e is 1.

All variables preferably have the preferred meanings.

Difunctional phenylene sulfides of Formula I, wherein at least one variable has one of the following meanings, are particularly preferred:
R$^1$, R$^2$ independently of each other in each case are H or Br,
R$^3$ is absent or is a C$_2$-C$_4$ alkylene radical,
R$^4$ is absent or is a C$_1$-C$_3$ alkylene radical,
R$^5$ is H,
a, b, c, d in each case are 0, and
e is 1.

All variables preferably have the particularly preferred meanings.

In all cases those compounds in which the vinyl sulfide groups are bound to the phenyl rings in each case in p-position relative to the S atom which bridges the phenyl rings are quite particularly preferred.

The difunctional phenylene sulfides of general formula I according to the invention can be obtained in a manner known per se. For example, the particularly preferred bis (4-vinylthiophenyl)sulfide can be prepared from the commercially available 4,4'-thiobis(benzenethiol). First of all the thioether formation is effected by reaction with excess 1,2-dichloroethane in the presence of KOH and tetrabutylammonium chloride at room temperature, wherein the corresponding bis[4-(2-chloroethylthiophenyl)sulfide forms, the dehydrohalogenation of which with KOH in water at elevated temperature, preferably at 85° C., leads to the bis(4-vinylthiophenyl)sulfide:

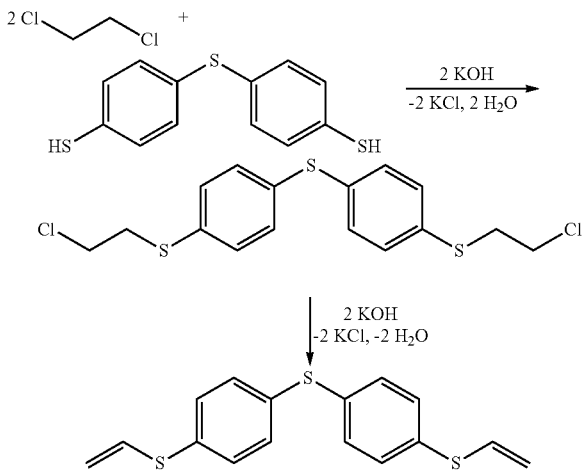

Preferred difunctional phenylene sulfides of general formula I are:

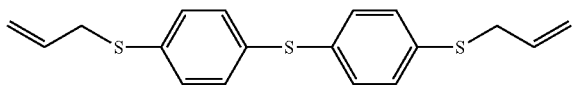

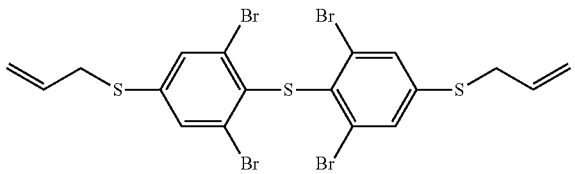

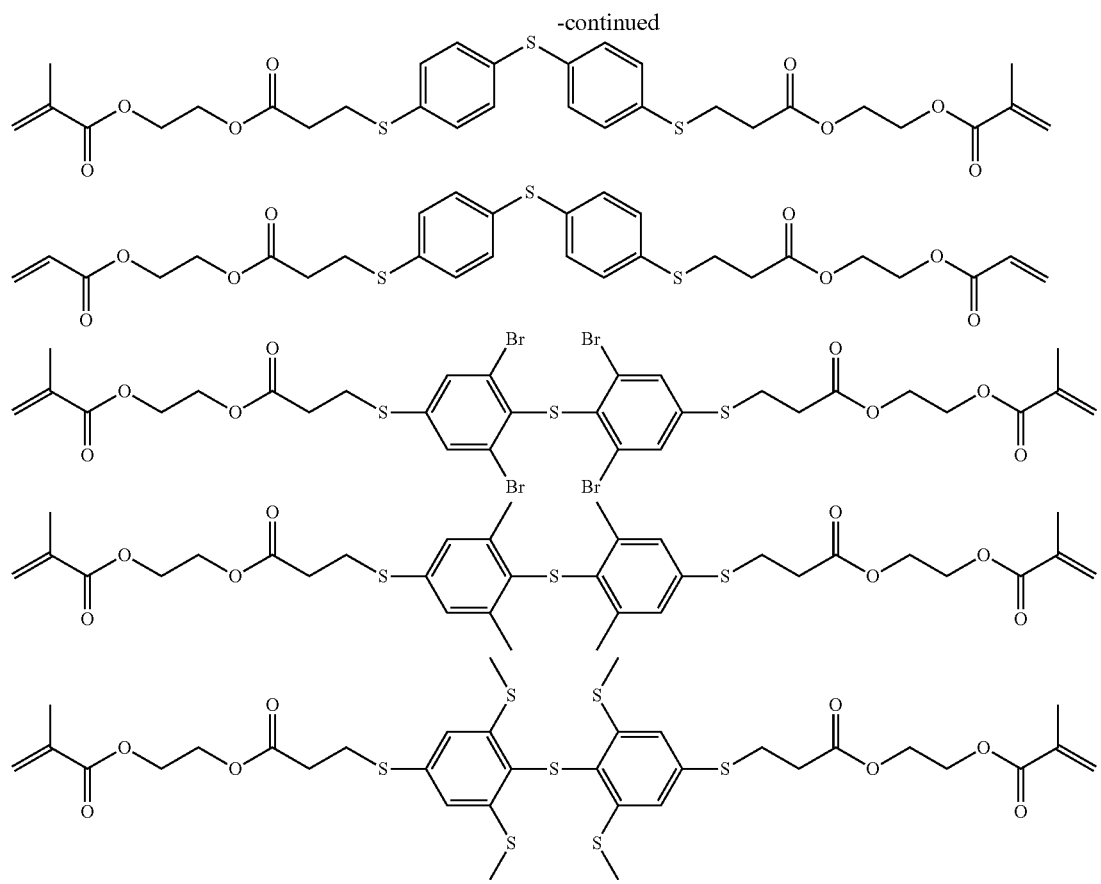
Particularly preferred difunctional phenylene sulfides of general formula I are:
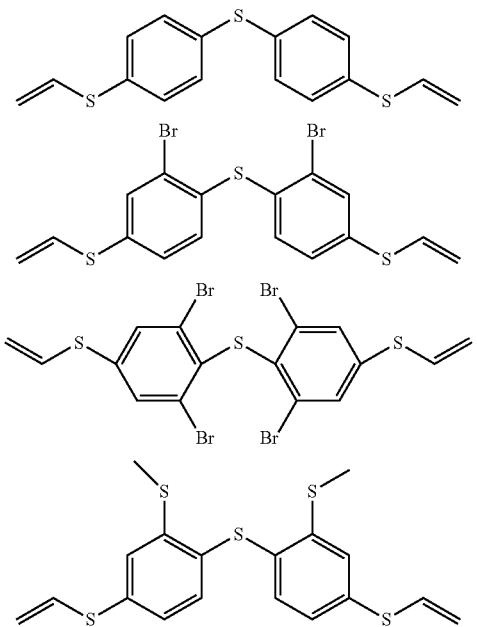
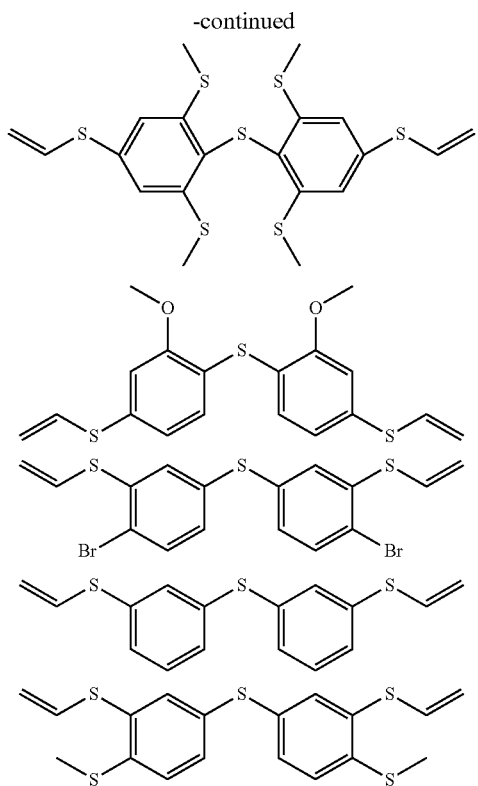

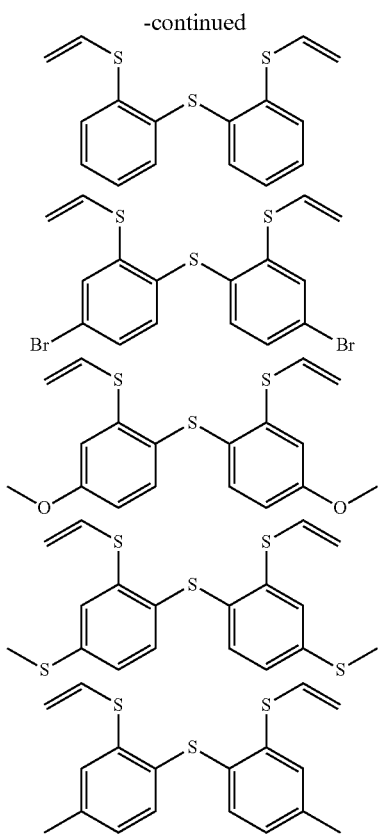

The monomers of Formula I are characterized by a low viscosity. They preferably have a viscosity of ≤3 Pas, preferably 5 to 2,000 mPas and particularly preferably 10 to 1,000 mPas, wherein the viscosity is determined using a capillary viscometer at a temperature of 23° C.

The difunctional phenylene sulfides of Formula I according to the invention are used alone or preferably mixed with at least one further radically polymerizable monomer for the preparation of dental materials. Materials which contain at least one mono- or multifunctional (meth)acrylate as radically polymerizable monomer are particularly preferred. By monofunctional (meth)acrylates are meant compounds with one radically polymerizable group, by multifunctional (meth)acrylates are meant compounds with two or more, preferably 2 to 4 radically polymerizable groups. According to a quite particularly preferred embodiment, the compositions according to the invention contain at least one dimethacrylate or a mixture of mono- and dimethacrylates. Materials which are to be cured intraorally preferably contain mono- and/or multifunctional methacrylates as radically polymerizable monomer.

Examples of particularly suitable mono- or multifunctional (meth)acrylates are methyl, ethyl, 2-hydroxyethyl, butyl, benzyl, tetrahydrofurfuryl and isobornyl methacrylate, p-cumylphenoxyethylene glycol methacrylate (CMP-1E), bisphenol A dimethacrylate, Bis-GMA (an addition product of methacrylic acid and bisphenol A diglycidyl ether), ethoxylated or propoxylated bisphenol A dimethacrylate, such as e.g. 2-[4-(2-methacryloyloxyethoxyethoxy)phenyl]-2-[4-(2-methacryloyloxyethoxy)phenyl]propane) (SR-348c, from Sartomer; contains 3 ethoxy groups) and 2,2-bis[4-(2-methacryloxypropoxy)phenyl]propane, UDMA (an addition product of 2-hydroxyethyl methacrylate and 2,2,4-trimethylhexamethylene diisocyanate), TMX-UDMA (an addition product of a mixture of HEMA and hydroxypropyl methacrylate (HPMA) with α,α,α',α'-tetramethyl-m-xylylene diisocyanate), di-, tri- or tetraethylene glycol dimethacrylate, trimethylolpropane trimethacrylate, pentaerythritol tetramethacrylate, as well as glycerol di- and trimethacrylate, 1,4-butanediol dimethacrylate, 1,10-decanediol dimethacrylate ($D_3MA$), 1,12-dodecanediol dimethacrylate, TCP and mixtures thereof. Particularly preferred monomers are benzyl, tetrahydrofurfuryl and isobornyl methacrylate, CMP-1E, 2,2-bis[4-(2-methacryloxypropoxy)phenyl]propane, Bis-GMA, UDMA, SR-348c, TCP, $D_3MA$ and mixtures thereof. Dental materials which contain Bis-GMA, UDMA, TMX-UDMA, TMX-UDMA $D_3MA$, TEGDMA, CMP-1E, TCP, SR-348c or a mixture thereof as radically polymerizable monomer are particularly preferred.

N-mono- or N-disubstituted acrylamides, such as e.g. N-ethylacrylamide or N,N-dimethacrylamide, bisacrylamides such as e.g. N,N'-diethyl-1,3-bis(acrylamido)-propane, 1,3-bis(methacrylamido)-propane, 1,4-bis(acrylamido)-butane, 1,4-bis(acryloyl)piperazine and mixtures thereof can advantageously also be used as radically polymerizable monomers.

It has surprisingly been found that the difunctional phenylene sulfides of general formula I can be copolymerized well with usual dental monomers and in particular with mono- or multifunctional (meth)acrylates and quite particularly with the above-named (meth)acrylates. This was not to be expected because the difunctional phenylene sulfides of Formula I represent π-electron-rich monomers, which are known to be capable only of poor radical copolymerization with (meth)acrylates. The copolymerizability is an important prerequisite for the preparation of dental materials.

The difunctional phenylene sulfides of Formula I are also characterized by a low polymerization shrinkage. This lies below 10 vol.-%, which is likewise an important criterion for dental applications.

According to the invention, monomers and monomer mixtures which have a refractive index which comes close to that of the filler used and thus allows a high translucence to be expected are preferred for the preparation of composites. Dental fillers usually have a refractive index of from approximately 1.523 to 1.550. Although the widely used Bis-GMA has a very advantageous refractive index in this respect ($n_D$=1.5512), its high viscosity makes it difficult to incorporate fillers and greatly restricts the maximum filler quantity. Usual diluent monomers usually have a refractive index of far below 1.50 and therefore, in addition to the sought reduction in viscosity, also bring about an undesired lowering of the refractive index of the monomer mixture. The difunctional phenylene sulfides of general formula I according to the invention are characterized, in contrast, by a low viscosity and a high refractive index. They therefore make it possible to adjust the viscosity of the monomer mixture without reducing the refractive index, or to adjust the refractive index without increasing the viscosity.

Compounds of Formula I that are preferred according to the invention have a refractive index of more than 1.57, preferably of from 1.575 to 1.75 and particularly preferably of from 1.58 to 1.72.

The refractive index is a substance constant, which depends on the wavelength of the light used, on the temperature, on the pressure and the purity of the substance. Unless otherwise indicated, by the refractive index is meant here the refractive index measured at 20° C. with the light of the yellow Na D line (λ=589 nm) ($n_D^{20}$ or $n_D$ for short).

The refractive index of liquid monomers and monomer mixtures can be determined by using a commercially available Abbe refractometer.

The materials according to the invention preferably contain at least one photoinitiator for the radical polymerization, particularly a photoinitiator which is active in a wavelength range from 400 to 500 nm.

Preferred photoinitiators are photosensitizers, above all of α-diketones, such as 9,10-phenanthrenequinone, 1-phenyl-propane-1,2-dione, diacetyl or 4,4'-dichlorobenzil or derivatives thereof, particularly preferably camphorquinone (CQ) and derivatives thereof, and mixtures thereof.

The photoinitiators are preferably used in combination with accelerators. Tertiary amines, such as e.g. tertiary aromatic amines, in particular N,N-dialkylanilines, -p-toluidines or -3,5-xylidines, p-(N, N-dialkylamino)-phenylethanol, -benzoic acid derivatives, -benzaldehyde, -phenylacetic acid ester and -phenylpropionic acid ester, are particularly suitable as accelerators. Specific examples of these are N,N-dimethylaniline, N,N-dimethyl-p-toluidine, N,N,3,5-tetramethylaniline, N,N-dimethylamino-p-benzaldehyde, p-(dimethylamino)-benzoic acid ethyl ester or p-(dimethylamino)-benzonitrile. Tertiary aliphatic amines, such as e.g. tri-n-butylamine, dimethylaminoethan-2-ol, triethanolamine, dimethylaminoethyl methacrylate, N,N-dimethyl-benzylamine, or heterocyclic amines, such as e.g. 1,2,2,6,6-pentamethylpiperidine, and amino acid derivatives, such as e.g. N-phenylglycine, are also suitable.

In compositions which contain acidic monomers, such as e.g. self-adhesive composites, amine-free accelerators are preferably used, such as e.g. sulfinic acids and sulfinates, borates, enolates, phosphines or other compounds which contain active hydrogen atoms, e.g. heterocyclic compounds such as morpholine derivatives or 1,3-dioxolanes.

Particularly preferred photoinitiators are acyl- or bisacylgermanium compounds, in particular the monoacyltrialkyl and bisacyldialkyl germanium compounds disclosed in EP 1 905 413 A1, such as e.g. benzoyltrimethylgermanium, bisbenzoyldiethylgermanium or bis(4-methoxybenzoyl)diethylgermanium. Acyl- and bisacylgermanium compounds have the advantage that they bleach after irradiation (bleaching effect) and thus do not impair the transparency of the cured materials. In addition, they are monomolecular photoinitiators, i.e. they do not require accelerators in order to achieve their full activity.

Further particularly preferred photoinitiators are acyl- or bisacylphosphine oxides, in particular the compounds described in EP 0 007 505, EP 0 073 413, EP 0 184 095 and EP 0 615 980. Preferred examples are the commercially available compounds 2,4,6-trimethylbenzoyldiphenylphosphine oxide (Lucirin® TPO, BASF) and bis(2,4,6-trimethylbenzoyl)phenylphosphine oxide (Irgacure® 819, Ciba). Acyl- and bisacylphosphine oxides likewise belong to the group of monomolecular photoinitiators and are characterized by a low self-absorption.

The materials according to the invention can additionally contain one or more further initiators for the radical polymerization, such as e.g. peroxides or hydroperoxides or redox initiator combinations, such as e.g. combinations of benzoyl peroxide with N,N-dimethyl-sym.-xylidine or N, N-dimethyl-p-toluidine, combinations of inorganic peroxides, above all potassium and ammonium peroxodisulfate, with reducing agents such as sulfite, hydrogen sulfite, thiosulfate, sulfinic acids, amines, enediols or Fe(II) salts, redox systems consisting of organic peroxides or hydroperoxides and reducing agents such as e.g. ascorbic acid, barbiturates, thioureas or sulfinic acids. Furthermore compounds of transition metals which have at least 2 stable valency stages can be used as transition metal redox catalysts. These are, above all, compounds of the elements copper, iron, vanadium, nickel or cobalt, wherein copper compounds are particularly preferred and they are preferably used as very organo-soluble compounds, such as e.g. as acetylacetonate, naphthenate or 2-ethylhexanoate.

The dental materials according to the invention can contain organic or preferably inorganic or organic-inorganic fillers, wherein particulate fillers are preferred. Preferred inorganic particulate fillers are powders of X-ray-opaque glasses with an average particle size of from 0.01 to 15 µm, preferably 0.10 to 5.0 µm; X-ray-opaque fillers, such as ytterbium trifluoride, with an average particle size of from 0.050 to 2.0 µm, preferably 0.10 to 1.0 µm; mixed oxides of $SiO_2$, $ZrO_2$, ZnO and/or $TiO_2$ with an average particle size of from 5 to 500 nm, preferably 20 to 200 nm; nanoparticulate fillers, such as tantalum(V) oxide, barium sulfate or mixed oxides of $SiO_2$ with ytterbium(III) oxide or tantalum(V) oxide with an average particle size of from 5 to 500 nm, preferably 20 to 200 nm.

In addition to the named fillers, the materials can contain fillers with a particle size of preferably <50 nm, particularly preferably <40 nm. The particle size preferably lies in the range of 10-50 nm and particularly preferably of 10-40 nm. Because of their small particle size, these fillers do not scatter visible light and thus have no influence on the translucence. Preferred examples of these fillers are pyrogenic silica and precipitated silica.

All particle sizes are weight-average. The light scattering decreases as the particle size decreases, but fillers with a small particle size have a greater thickening effect. According to the invention, therefore, fillers with a particle size in the range of from 100 nm to 5 µm and in particular in the range of from 200 nm to 2 µm are preferred.

The fillers are preferably surface-modified, particularly preferably by silanization, in particular with 3-methacryloy-loxypropyltrimethoxysilane. The silanization has no measurable influence on the refractive index of the filler.

Dental materials which contain a barium or strontium aluminium borosilicate glass, pyrogenic silica, a mixed oxide of $SiO_2$ and $ZrO_2$, or ytterbium fluoride or a mixture thereof as filler are particularly preferred.

Optionally, the compositions used according to the invention can contain further additives, above all stabilizers, such as e.g. polymerization stabilizers, dyestuffs, antibacterial agents, fluoride-ion-releasing additives, optical brighteners, fluorescent agents, UV absorbers, substances for improving fracture toughness and/or effect agents.

The materials according to the invention preferably contain at least one basic component, preferably a tertiary amine as stabilizer. This prevents a premature spontaneous cationic polymerization of the π-electron-rich vinyl sulfide groups of the difunctional phenylene sulfides of general formula I. The basic component is preferably added in a quantity of from 10 to 1000 ppm.

According to the invention, radically polymerizable dental materials are preferred which contain
(a) at least one difunctional phenylene sulfide according to Formula I,
(b) at least one photoinitiator for the radical polymerization,
(c) preferably at least one further radically polymerizable monomer, and
(d) preferably at least one filler.

Dental materials are particularly preferred which contain (a) 0.1 to 95 wt.-%, preferably 1 to 80 wt.-% and particularly preferably 5 to 70 wt.-% difunctional phenylene sulfides of Formula I,
(b) 0.01 to 5 wt.-%, particularly preferably 0.01 to 3.0 wt.-% and particularly preferably 0.1 to 1.0 wt.-% initiator,
(c) 0 to 80 wt.-%, preferably 1 to 60 wt.-% and particularly preferably 10 to 50 wt.-% further radically polymerizable monomer, and
(d) 0 to 85 wt.-%, preferably 10 to 85 wt.-% and particularly preferably 30 to 85 wt.-% filler.

The filling level is adjusted to the desired intended use of the material. Filling composites preferably have a filler content of 25-85 wt.-% and composite cements have a filler content of 25-70 wt.-%.

All indications of quantity (wt.-% and ppm) herein relate to the total mass of the dental material, unless otherwise specified.

Those dental materials which consist of the named substances are particularly preferred.

In addition, those materials in which the individual components in each case are selected from the above-named preferred and particularly preferred substances are preferred.

Dental materials which contain Bis-GMA, UDMA, TMX-UDMA, $D_3MA$, TEGDMA, CMP-1E, TCP, SR-348c or a mixture thereof as radically polymerizable monomer (c) are quite particularly preferred. Furthermore, dental materials which contain a barium or strontium aluminium borosilicate glass, pyrogenic silica, a mixed oxide of $SiO_2$ and $ZrO_2$, or ytterbium fluoride or a mixture thereof as filler (d) are preferred. Dental materials which contain at least one of the named monomers as monomer (c) and at least one of the named fillers as filler (d) are particularly advantageous.

The materials according to the invention are particularly suitable as dental materials, in particular as dental cements, filling composites and veneering materials, and as materials for the production of prosthetics, artificial teeth, inlays, onlays, crowns and bridges. The dental materials are primarily suitable for intraoral use by the dentist to restore damaged teeth, i.e. for therapeutic use, e.g. as dental cements, filling composites and veneering materials. However, they can also be used extraorally, for example in the production or repair of dental restorations, such as prosthetics, artificial teeth, inlays, onlays, crowns and bridges.

The materials according to the invention are also suitable for producing shaped bodies for dental, but also for non-dental, purposes which can be produced e.g. by means of casting, compression moulding and, in particular, by generative processes such as 3D printing.

In addition the invention relates to the use of bis(vinylthiophenyl)sulfides of Formula I for the preparation of dental materials.

The invention is explained in more detail below with reference to examples.

EXAMPLES

Example 1

Synthesis of bis(4-vinylthiophenyl)sulfide

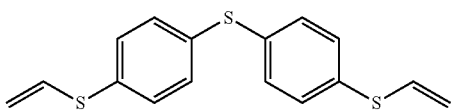 [SMILES: C=CSc1ccc(Sc2ccc(SC=C)cc2)cc1]

To synthesize bis(4-vinylthiophenyl)sulfide, 4,4'-thiobis(benzenethiol) was first reacted with an excess of 1,2-dichloroethane in the presence of KOH and tetrabutylammonium chloride at room temperature (23° C.). The bis[4-(2-chloroethylthiophenyl)sulfide obtained was dehydrohalogenated with KOH in water at 85° C. to form bis(4-vinylthiophenyl)sulfide. Bis(4-vinylthiophenyl)sulfide was obtained as a colourless, low-viscosity liquid at room temperature, with a viscosity η of only 17 mPa s (23° C.). The refractive index $n_D$ is 1.695 and the polymerization shrinkage $\Delta_P V$ is −7.8 vol.-%. The polymerization shrinkage was measured in accordance with DIN 13907: "Dentistry: Polymerization shrinkage of filling materials".

Example 2

Monomer Mixtures with a Monomer According to the Invention

Starting from bis(4-vinylthiophenyl)sulfide and the frequently used dental diluent monomer triethylene glycol dimethacrylate (TEGDMA), various monomer mixtures were prepared and their refractive indices were determined (Table 1). The properties of TEGDMA are: η=10 mPa s (23° C.), $n_D$=1.461 and $\Delta_{P\ V}$=−14.3 vol.-%.

The results in Table 1 demonstrate that the monomer according to the invention is very suitable for the preparation of mixtures with a much higher refractive index starting from usual dental diluent monomers which exhibit a low refractive index.

TABLE 1

| Refractive indices of mixtures of bis(4-vinylthiophenyl)sulfide and TEGDMA | |
|---|---|
| Monomer mixture [wt.-%/wt.-%] | Refractive index |
| TEGDMA | 1.461 |
| Bis(4-vinylthiophenyl)sulfide/TEGDMA: 10:90 | 1.482 |
| Bis(4-vinylthiophenyl)sulfide/TEGDMA: 20:80 | 1.504 |
| Bis(4-vinylthiophenyl)sulfide/TEGDMA: 40:60 | 1.548 |
| Bis(4-vinylthiophenyl)sulfide/TEGDMA: 50:50 | 1.572 |
| Bis(4-vinylthiophenyl)sulfide | 1.695 |

Example 3

Light-Curing Resin

To prepare a light-curing resin, 5.0 g bis(4-vinylthiophenyl)sulfide was mixed with 4.95 g TEGDMA and the photoinitiator Ivocerin® (bis(4-methoxybenzoyl)diethylgermanium (Ivoclar Vivadent AG), 50 mg). From the mixture, test pieces were prepared which were irradiated for 3 minutes twice with a dental light source (Spectramat®, Ivoclar Vivadent AG) and thereby cured. In accordance with the ISO standard ISO-4049 (Dentistry—Polymer-based filling, restorative and luting materials), the flexural strength (FS) and the flexural modulus (FM) were determined after 24 h of storage of the test pieces at room temperature (RT) or after 24 h or 1 week (7 d) of storage in water at 37° C. (WS) (Table 2):

TABLE 2

Mechanical properties of a mixture of bis(4-vinylthiophenyl)sulfide and TEGDMA after light curing

|  | 24 h RT | 24 h WS | 7 d WS |
|---|---|---|---|
| FS (MPa) | 82.4 ± 10.3 | 96.9 ± 13.3 | 78.6 ± 9.0 |
| FM (GPa) | 2.36 ± 0.21 | 2.62 ± 0.19 | 2.71 ± 0.15 |

The results of the mechanical investigations in Table 2 show that the monomer according to the invention bis(4-vinylthiophenyl)sulfide allows surprisingly good radical copolymerization with a dimethacrylate. It was not to be expected that π-electron-rich difunctional phenylene sulfides of Formula I could be radically copolymerized with methacrylates.

Example 4

Light-Curing Composite

A composite was prepared from the following components: 17.60 g bis(4-vinylthiophenyl)sulfide, 17.42 g TEGDMA, 0.18 g Ivocerin® (from Ivoclar Vivadent AG, Liechtenstein), 44.80 g of the silanized pyrogenic silica OX-50 (from Degussa AG, Germany) and 20.00 g ytterbium trifluoride $YbF_3$ (from Sukgyung, South Korea). From the colourless pastes, test pieces corresponding to Example 3 were analogously prepared and cured, and the flexural strength and flexural modulus were determined (Table 3).

TABLE 3

Mechanical properties of a light-curing composite of bis(4-vinylthiophenyl)sulfide, TEGDMA and dental fillers.

|  | 24 h RT | 24 h WS | 7 d WS |
|---|---|---|---|
| FS (MPa) | 113.1 ± 7.7 | 107.3 ± 16.0 | 109.5 ± 10.3 |
| FM (GPa) | 7.81 ± 0.44 | 7.31 ± 0.65 | 7.62 ± 0.48 |

The results in Table 3 demonstrate that dental light-curing composites with very good mechanical properties can be prepared with the bis(4-vinylthiophenyl)sulfide according to the invention mixed with the dimethacrylate diluent TEGDMA. This is proof that the π-electron-rich difunctional phenylene sulfides of Formula I also allow very good radical copolymerization with methacrylates in the presence of filler.

The invention claimed is:

1. A dental material, comprising at least one radically polymerizable, difunctional phenylene sulfide according to Formula I, Formula I -continued in which
X, Y independently of each other in each case are absent or are O or $NR^6$,
$R^1$, $R^2$ independently of each other in each case are H, a linear or branched $C_1$ to $C_{10}$ alkyl radical, $-OR^7$, $-SR^8$, Cl or Br,
$R^3$ is absent or is a $C_1$-$C_{10}$ alkylene radical, which can be interrupted by O or S,
$R^4$ is absent or is a $C_1$-$C_{10}$ alkylene radical, which can be interrupted by O or S,
$R^5$ is H or a $C_1$-$C_5$ alkyl radical,
$R^6$, $R^7$, $R^8$ independently of each other in each case are H or a linear or branched $C_1$ to $C_{10}$ alkyl radical,
a, b, c, d independently of each other in each case are 0 or 1 and
e is 1 or 2,
at least one mono- or multifunctional (meth)acrylate, and
at least one filler in an amount of 65-85% of the dental material.

2. The dental material according to claim 1, wherein the variables have the following meanings:
X, Y independently of each other in each case are absent or are O,
$R^1$, $R^2$ independently of each other in each case are H or Br, $CH_3$, $SCH_3$, $OCH_3$,
$R^3$ is absent or is a $C_2$-$C_4$ alkylene radical,
$R^4$ is absent or is a $C_1$-$C_3$ alkylene radical,
$R^5$ is H or $CH_3$,
a, b, c, d independently of each other in each case are 0 or 1, and
e is 1.

3. The dental material according to claim 1, wherein the variables have the following meanings:
$R^1$, $R^2$ independently of each other in each case are H or Br,
$R^3$ is dispensed with or is a $C_2$-$C_4$ alkylene radical,
$R^4$ is dispensed with or is a $C_1$-$C_3$ alkylene radical,
$R^5$ is H,
a, b, c, d in each case are 0, and
e is 1.

4. The dental material according to claim 1, wherein the difunctional *phenylene* sulfide of Formula I has a viscosity of 3 Pas, measured using a capillary viscometer at a temperature of 23° C.

5. The dental material according to claim 4, wherein the viscosity is in the range of 5 to 2,000 mPas, measured using a capillary viscometer at a temperature of 23° C.

6. The dental material according to claim 1, wherein the difunctional phenylene sulfide of Formula I has a refractive index of more than 1.57, measured at 20° C. with the light of the yellow Na D line (λ=589 nm).

7. The dental material according to claim 6, wherein the refractive index is in the range of from 1.575 to 1.75, measured at 20° C. with the light of the yellow Na D line (λ=589 nm).

8. The dental material according to claim 1, which additionally contains at least one initiator for the radical polymerization, wherein the initiator comprises a photoinitiator.

9. The dental material according to claim 1, wherein the at least one mono- or multifunctional (meth)acrylate comprises Bis-GMA, UDMA, TMX-UDMA, $D_3MA$, TEGDMA, CMP-1E, TCP, SR-348c or a mixture thereof.

10. The dental material according to claim 1, wherein the at least one filler comprises an organic, inorganic or organic-inorganic filler.

11. The dental material according to claim 10, wherein the at least one filler comprises a barium or strontium aluminium borosilicate glass, pyrogenic silica, a mixed oxide of $SiO_2$ and $ZrO_2$, ytterbium fluoride or a mixture thereof.

12. The dental material according to claim 1, which contains
    (a) 5 to 70 wt.-% of at least one difunctional phenylene sulfide according to Formula I,
    (b) 0.1 to 3.0 wt.-% of at least one initiator for the radical polymerization,
    (c) 10 to 50 wt.-% of at least one further radically polymerizable monomer, in each case relative to the total mass of the material, and
    (d) 65 to 85 wt.-% filler.

13. The dental material according to claim 1 for therapeutic use as a dental cement, filling composite or veneering material.

14. A method of using the dental material according to claim 1 for the extraoral production or repair of dental restorations, prosthetics, artificial teeth, inlays, onlays, crowns or bridges comprising
    3D printing the dental material into one or more of the dental restorations, prosthetics, artificial teeth, inlays, onlays, crowns or bridges.

15. A method of using a difunctional phenylene sulfide according to Formula I of claim 1 for the preparation of a dental material comprising
    3D printing the difunctional phenylene sulfide according to Formula I into the dental material.

16. The dental material according to claim 4, wherein the viscosity is in the range of 10 to 1,000 mPas, measured using a capillary viscometer at a temperature of 23° C.

17. The dental material according to claim 6, wherein the refractive index is in the range of from 1.58 to 1.72, measured at 20° C. with the light of the yellow Na D line ($\lambda$=589 nm).

* * * * *